US 7,841,717 B2

(12) United States Patent
Ito et al.

(10) Patent No.: US 7,841,717 B2
(45) Date of Patent: Nov. 30, 2010

(54) OPHTHALMOLOGIC APPARATUS

(75) Inventors: Ryousuke Ito, Tokyo (JP); Takeshi Nakamura, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/320,926

(22) Filed: Feb. 9, 2009

(65) Prior Publication Data
US 2009/0207378 A1    Aug. 20, 2009

(30) Foreign Application Priority Data
Feb. 15, 2008    (JP)    ............................. 2008-034542

(51) Int. Cl.
*A61B 3/10* (2006.01)
*A61B 3/14* (2006.01)
*A61B 3/00* (2006.01)

(52) U.S. Cl. .................... 351/205; 351/206; 351/245

(58) Field of Classification Search .......... 351/205–246
See application file for complete search history.

(56) References Cited

U.S. PATENT DOCUMENTS

| 6,409,344 | B1 * | 6/2002 | Hayashi | 351/208 |
| 7,123,751 | B1 * | 10/2006 | Fujieda | 382/115 |
| 7,370,966 | B2 * | 5/2008 | Fukuma et al. | 351/208 |
| 7,413,305 | B2 * | 8/2008 | Baumann et al. | 351/208 |
| 2005/0117116 | A1 * | 6/2005 | Murakami | 351/211 |

FOREIGN PATENT DOCUMENTS

| EP | 1854400 | 11/2007 |
| JP | 2001-187024 | 7/2001 |
| JP | 2007-282671 | 11/2007 |
| JP | 2007-282672 | 11/2007 |

OTHER PUBLICATIONS

European Search Report dated May 11, 2009, issued on the corresponding European patent application No. 09000879.8.
The CT-90A non-contact type tonometer, TOPCON Corp. Online Catalogue, retrieved on Feb. 6, 2008 (4 sheets).

* cited by examiner

*Primary Examiner*—Mohammed Hasan
(74) *Attorney, Agent, or Firm*—Edwards Angell Palmer & Dodge LLP

(57) ABSTRACT

An opthalmologic apparatus having a setting part configured to acquire position information of a first examining part at the time of execution of a first examination and set a movable range of a second examining part in a direction of a second working distance based on the position information and distance information. This opthalmologic apparatus controls so that an examining unit moves within the movable range set based on the position information of the first examining part and the distance information when an examination by the examining unit is switched from the first examination to a second examination. Accordingly, it is possible to set an accurate movable range with respect to the position of the eye of a subject, and it is also possible to increase safety by preventing the examining part from coming in contact with the subject.

13 Claims, 9 Drawing Sheets

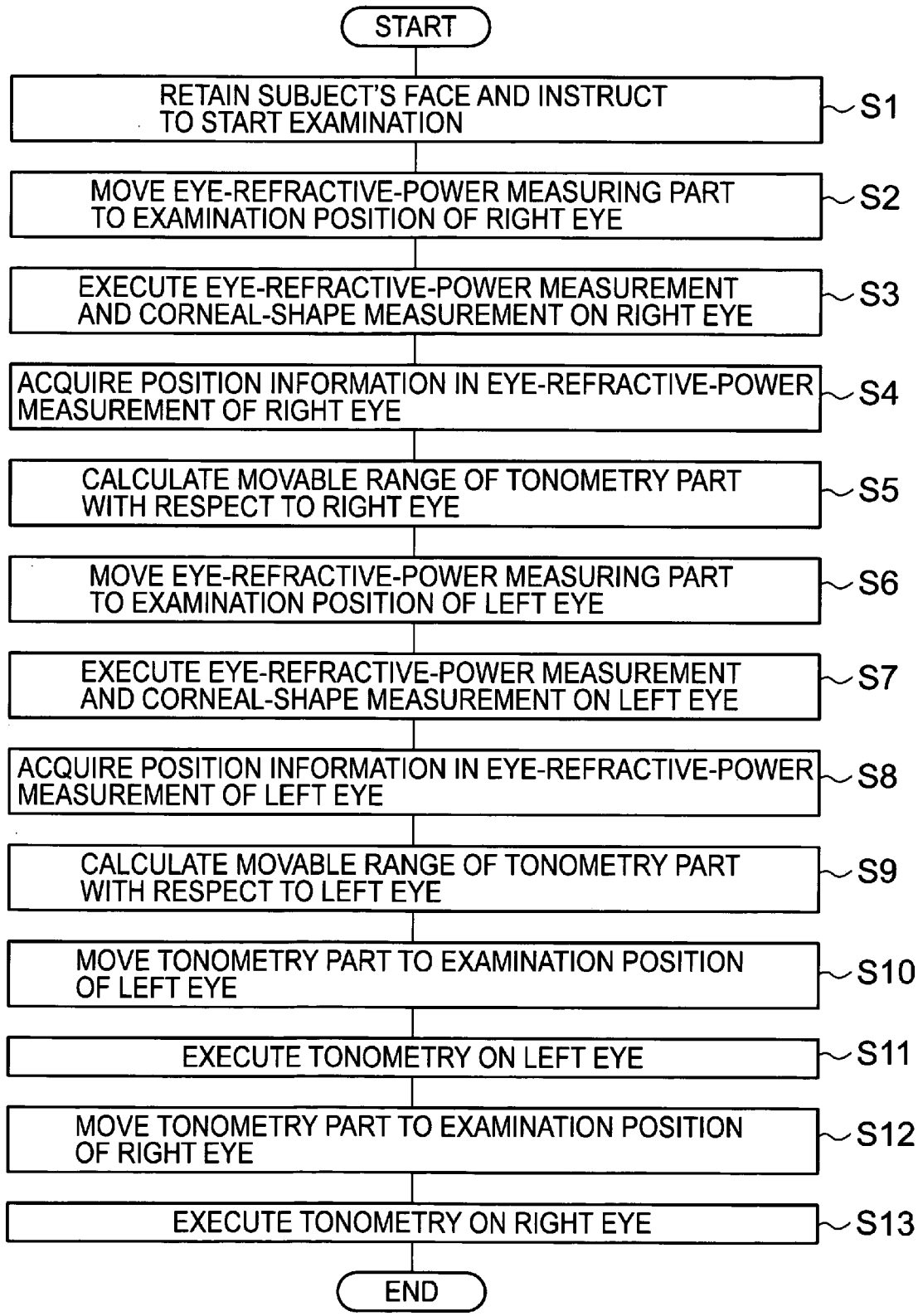

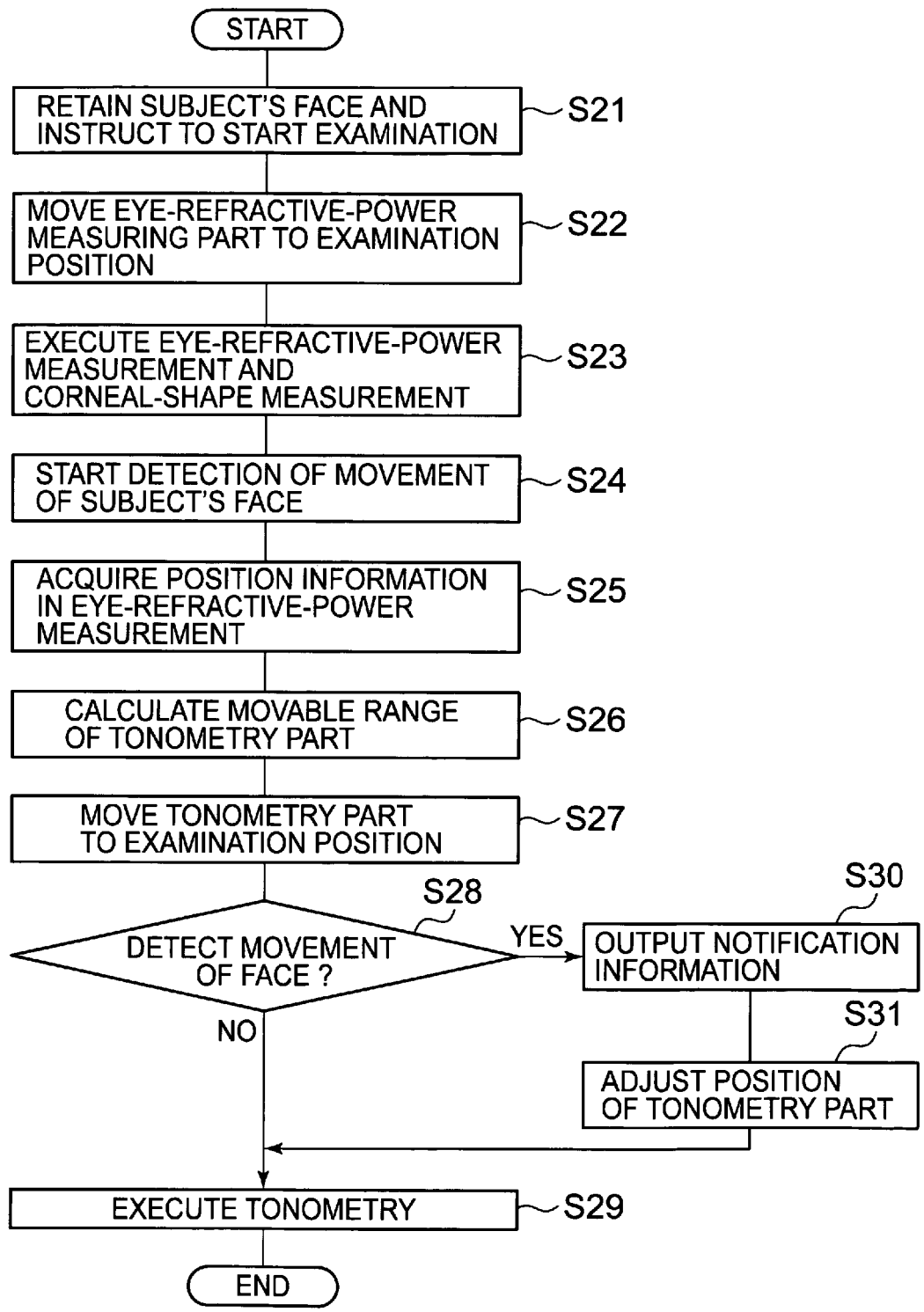

OPHTHALMOLOGIC APPARATUS

BACKGROUND OF THE INVENTION

1. Field of the Invention

The present invention relates to an ophthalmologic apparatus that executes a plurality of examinations on an eye.

2. Description of the Related Art

As an ophthalmologic apparatus that executes a plurality of examinations on an eye, an apparatus described in Japanese Unexamined Patent Application Publication No. 2007-282671 is known, for example. This ophthalmologic apparatus incorporates a first measuring part (an eye-refractive-power/corneal-shape measuring part) and a second measuring part (a tonometry part). These measuring parts are arranged next to each other in the vertical direction.

A working distance in tonometry is generally shorter than a working distance in eye-refractive-power measurement and corneal-shape measurement. For example, the former working distance is set to approximately 11 mm, and the latter working distance is set to approximately 35 mm.

In tonometry with a rather short working distance as described above, there is a risk that a nozzle for ejecting air comes in contact with a subject. The ophthalmologic apparatus according to JP-A 2007-282671 is configured to avoid contact with the subject by moving the tonometry part in a direction of the working distance (an anteroposterior direction with respect to the eye) when switching from the eye-refractive-power measurement, etc., to the tonometry.

Conventional tonometers also have various innovations to prevent contact with the subject. For example, Japanese Unexamined Patent Application Publication No. 2001-187024 describes a tonometer having a function of detecting the proximity to the subject and moving a measuring head.

Further, a tonometer disclosed on the Internet (URL: http://www.topcon.co.jp/eyecare/pdf/ct_90a.pdf) as a non-contact type tonometer CT-90A by TOPCON Corporation in an online catalogue (retrieved on Feb. 6, 2008) has a function of automatically stopping the movement of the apparatus when the apparatus is too close to the cornea, and a function of notifying (with a display or an alarm) that the apparatus is too close to the cornea.

In the eye-refractive-power measurement and the corneal-shape measurement, the working distances are relatively long. Therefore, the abovementioned safety measurements are not taken in general.

It is also possible to configure the measuring unit to move at a high speed in order to reduce a time for switching between the right and left eyes. However, if the weight of the measuring unit, etc. is taken into consideration, the safety in the subject may be lowered by decrease of the accuracy of the operation of moving the measuring unit, and the subject may feel anxious or surprised due to the sound generated during the movement.

In the ophthalmologic apparatus capable of executing a plurality of examinations, the following problems arise even when the aforementioned conventional art is incorporated.

First, the ophthalmologic apparatus described in JP-A 2007-282671 automatically moves the tonometry part toward the eye when shifting from the measurement of the eye refractive power, etc., to the measurement of the ocular tension (i.e., when moving the measuring head in the vertical direction). Consequently, the tonometry part is placed 24 mm (subtracting 11 mm from 35 mm) closer to the eye than the eye-refractive-power/corneal-shape measuring part.

Before executing the tonometry, it is required to align the tonometry part with the eye. During the alignment, the measuring head (tonometry part) may be moved in the anteroposterior direction. Here, if the movable range in the anteroposterior direction cannot be set as in the ophthalmologic apparatus described in JP-A 2007-282671, the nozzle may hit the eye. Specifically, the ophthalmologic apparatus of JP-A 2007-282671 can prevent contact with the eye when the measuring head is moved in the vertical direction, but cannot effectively prevent contact with the eye during the alignment.

Further, even if the technology of JP-A 2001-187024 or the CT-90A non-contact type tonometer described on the Internet (URL: http://www.topcon.co.jp/eyecare/pdf/ct_90a.pdf) by TOPCON Corporation in the online catalogue (retrieved on Feb. 6, 2008) is applied, it is necessary to manually set the movable range of the measuring head, whereby problems arise such as drop in examination efficiency and cumbersome operation. Specifically, when examining both the right and left eyes, it is necessary to set the movable range for each of the eyes. Further, there is concern that setting of the movable range is forgotten or setting of the movable range is omitted in favor of optimizing the examination efficiency.

SUMMARY OF THE INVENTION

The present invention solves the aforementioned problems, and an object of the present invention is to provide an opthalmologic apparatus by which is it possible to increase the safety in the eye by automatically setting the movable range of the measuring head.

An embodiment of an ophthalmologic apparatus according to the present invention will be described. The ophthalmologic apparatus has a first examining part, a second examining part, a driver, a storage, a setting part, and a controller. The first examining part executes a first examination at a first working distance on an eye. The second examining part executes a second examination on the eye at a second working distance shorter than the first working distance. The driver moves the first examining part and the second examining part. The storage previously stores distance information including the first working distance and a distance between the second examining part and the eye in the second examination. The setting part acquires position information of the first examining part when the first examination is executed, and sets a movable range of the second examining part in a direction of the second working distance based on the position information and the distance information. The controller controls the driver to move the second examining part only within the movable range. Furthermore, the ophthalmologic apparatus executes the second examination after executing the first examination.

According to the embodiment of the ophthalmologic apparatus of the present invention, it is possible to set the movable range of the second examining part in the direction of the second working distance based on the position information of the first examining part when executing the first examination and based on the previously stored distance information, and it is possible to move the second examining part only within the movable range. Therefore, it is possible to increase the safety in the eye.

BRIEF DESCRIPTION OF THE DRAWINGS

FIG. 8 is a flowchart showing an example of the operation in the embodiment of the ophthalmologic apparatus according to the present invention.

FIG. 9 is a flowchart showing an example of the operation in the embodiment of the ophthalmologic apparatus according to the present invention.

DETAILED DESCRIPTION OF THE EMBODIMENT

An embodiment of an ophthalmologic apparatus according to the present invention will be described in detail with reference to the drawings.

[Configuration]

Figure 1:
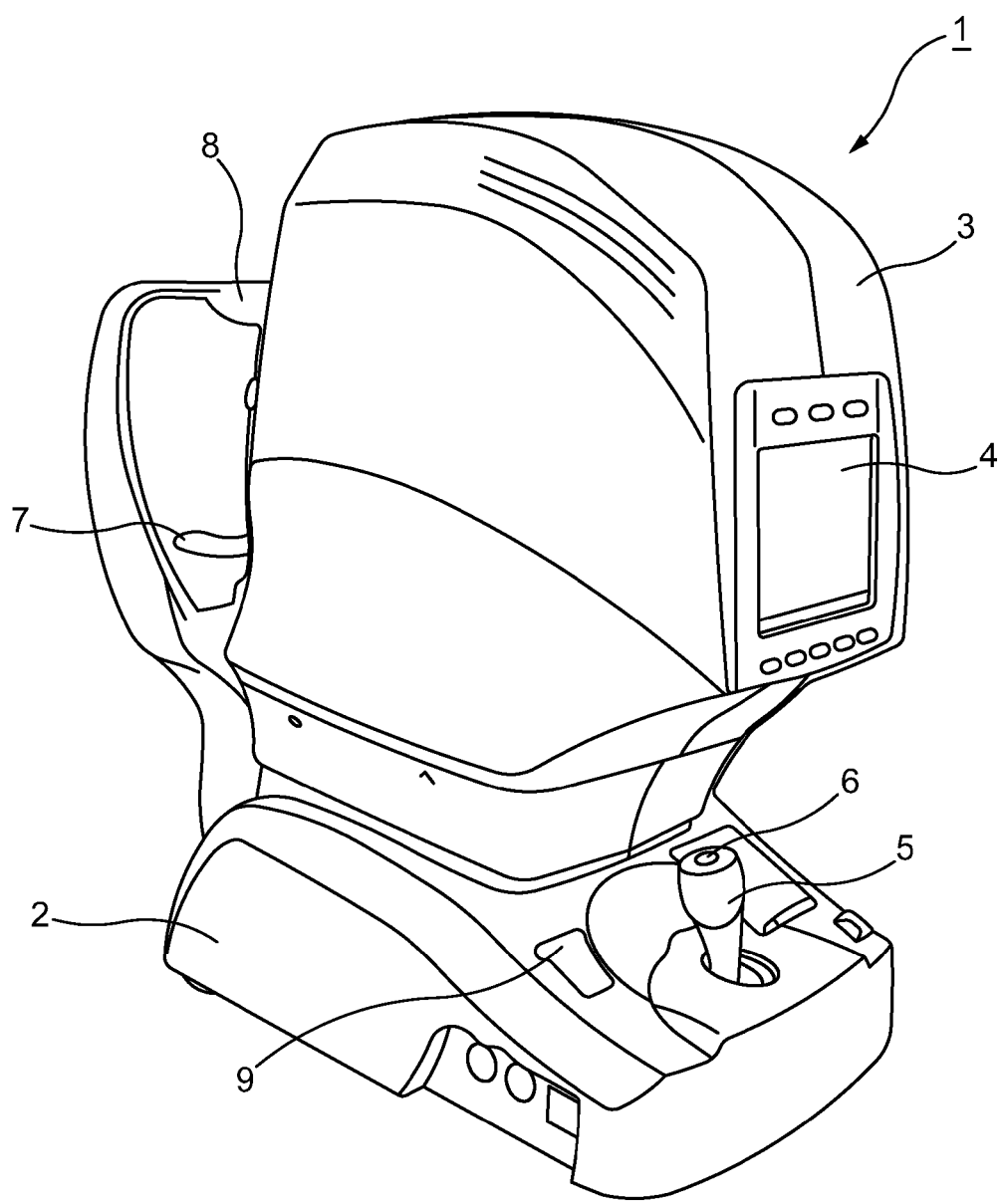
FIG. 1 is a schematic perspective view showing an example of the exterior configuration in an embodiment of an ophthalmologic apparatus according to the present invention.

FIGS. 1 to 6 show a configuration example of the ophthalmologic apparatus according to the present embodiment. The exterior of an ophthalmologic apparatus 1 is shown in FIG. 1. As in the conventional technique, the ophthalmologic apparatus 1 includes a base 2, a measuring head 3, a display 4, a control lever 5, a measurement switch 6, a jaw rest 7, a forehead rest 8, a jaw-rest moving switch 9, etc.

A subject puts his/her jaw on the jaw rest 7 and faces the measuring head 3 with his/her forehead contact with the forehead rest 8.

The jaw rest 7 and/or the forehead rest 8 is an example of a "retaining part" that retains the face of the subject. An operator operates the jaw-rest moving switch 9 to vertically move the jaw rest 7, thereby adjusting the position of the face of the subject. It is also possible to configure to move the forehead rest 8. The operator examines an eye while being positioned on a side where the display 4 and the control lever 5 are disposed. Further, in the case of executing eyelid opening on the subject, the operator may be positioned along the side face of the ophthalmologic apparatus 1.

Below, a vertical direction, an anteroposterior direction and a horizontal direction in this specification will be defined. (1) The vertical direction is the vertical direction. (2) The anteroposterior direction is a direction that is orthogonal to the vertical direction and that connects the operator's side and the subject's side. In other words, the anteroposterior direction is a direction that is orthogonal to the vertical direction and that connects the side of the display 4 and the side of the jaw rest 7. Here, a direction toward the subject's side is defined as the forward direction, and a direction opposite thereto is defined as the backward direction. (3) The horizontal direction is a direction orthogonal to both the vertical direction and the anteroposterior direction. Here, a direction from the right eye of the subject toward the left eye is defined as the leftward direction, and a direction opposite thereto is defined as the rightward direction.

As in the conventional technique, the base 2 houses a calculation control circuit, a storing device, a power supply circuit, etc.

The measuring head 3 is configured to be movable in the vertical, anteroposterior and horizontal directions, i.e., movable three-dimensionally with respect to the base 2. The measuring head 3 is moved by a drive mechanism 10, which will be described later. The measuring head 3 is moved by the drive mechanism 10 at the time of alignment with the eye, switching of an examination method, switching of an examination object from one eye to the other eye, advance to a working distance in accordance with the examination method, and retreat to a safe distance at the time of the abovementioned switching.

The display 4 displays an image such as an anterior segment image of an eye. Further, the display 4 displays various kinds of examination information such as patient information, examination conditions and examination results. The display 4 may be a touch panel display. In this case, various kinds of software keys are displayed on the display 4. The operator can cause the ophthalmologic apparatus 1 to execute a desired operation by pressing the software keys.

The control lever 5 is operated, for example, to manually move the measuring head 3. The measurement switch 6 is operated, for example, to execute a measurement on the eye. Switches are also disposed around the display 4 (above and below in FIG. 1). These switches are used, for example, at the time of alignment with the eye and adjustment of the display 4.

[Drive Mechanism]

Figure 2:
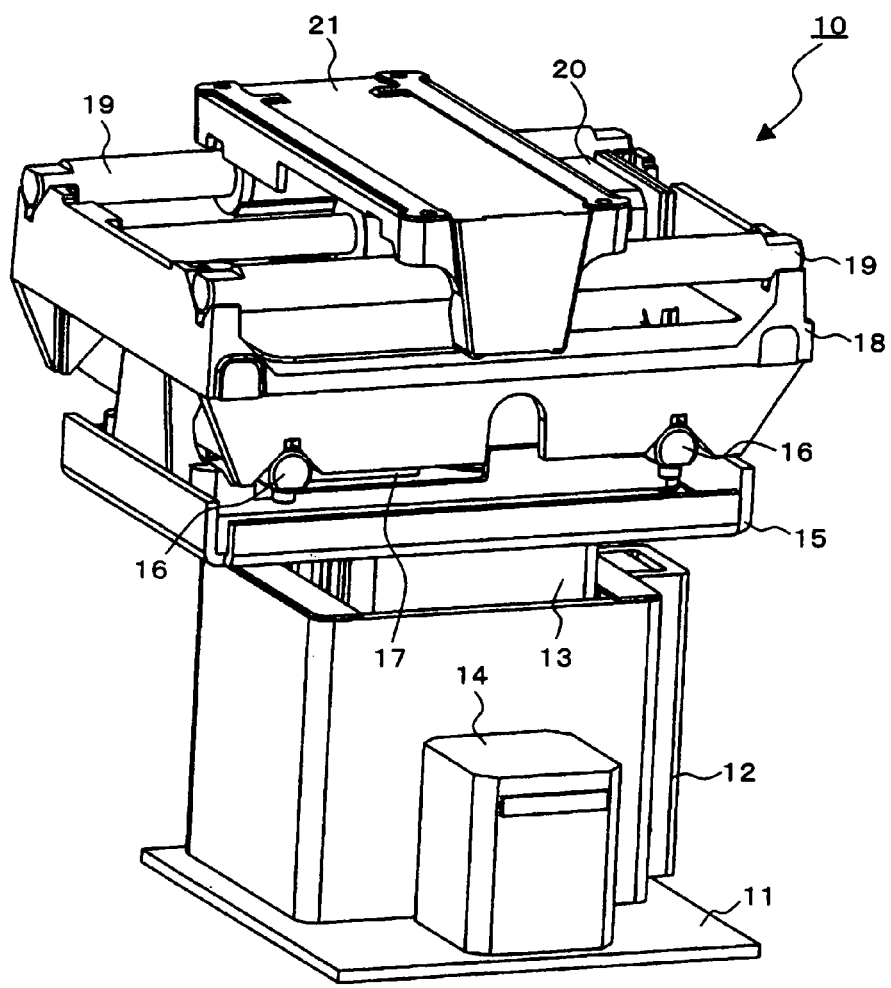
FIG. 2 is a schematic perspective view showing an example of the configuration of a drive mechanism in the embodiment of the ophthalmologic apparatus according to the present invention.

The drive mechanism 10 shown in FIG. 2 is provided with a configuration for moving the measuring head 3 in the vertical, anteroposterior and horizontal directions. The drive mechanism 10 is housed in the base 2. A bottom plate 11 is fixedly installed in the base 2. A supporting part 12 is fixedly attached to the top face of the bottom plate 11. The supporting part 12 has a hollow part. A support column 13 is disposed in the hollow part. A vertical drive motor 14 is fixedly placed on the top face of the bottom plate 11.

The vertical drive motor 14 includes an actuator such as a stepping motor (may be referred to as a pulse motor). A driving force generated by the vertical drive motor 14 is conveyed by a driving-force conveying mechanism, which is not illustrated, including gears, etc., to move the support column 13 in the vertical direction. A vertically moving stage 15 is fixedly attached to the upper end of the support column 13. The vertically moving stage 15 moves in the vertical direction together with the support column 13.

Anteroposterior rails 16 are disposed near the horizontal end parts of the top face of the vertically moving stage 15, respectively.

Each of the anteroposterior rails 16 is disposed so that a longitudinal direction thereof is along the anteroposterior direction. An anteroposterior moving stage 18 is mounted on the anteroposterior rails 16 so as to be movable in the anteroposterior direction.

Furthermore, on the top face of the vertically moving stage 15, an anteroposterior drive motor 17 is provided. The anteroposterior drive motor 17 includes an actuator such as a stepping motor. A driving force generated by the anteroposterior drive motor 17 is conveyed by a driving-force conveying mechanism, which is not illustrated, to move the anteroposterior moving stage 18 along the anteroposterior rails 16. The anteroposterior moving stage 18 is thereby moved in the anteroposterior direction with respect to the vertically moving stage 15.

Near the anteroposterior end parts of the top face of the anteroposterior moving stage 18, horizontal rails 19 are disposed. Each of the horizontal rails 19 is placed so that a longitudinal direction thereof is along the horizontal direction. A horizontal moving stage 21 is mounted on the horizontal rails 19 so as to be movable in the horizontal direction.

Furthermore, a horizontal drive motor 20 is disposed on the top face of the anteroposterior moving stage 18. The horizontal drive motor 20 includes an actuator such as a stepping motor. A driving force generated by the horizontal drive motor 20 is conveyed by a driving-force conveying mechanism, which is not illustrated, to move the horizontal moving stage 21 along the horizontal rails 19. The horizontal moving stage 21 is thereby moved in the horizontal direction with respect to the anteroposterior moving stage 18.

On the horizontal moving stage 21, the measuring head 3 is mounted. According to the drive mechanism 10, it is possible to separately move the measuring head 3 in the vertical direction, the anteroposterior direction and the horizontal direction.

[Measuring Head]

The measuring head 3 is provided with a plurality of examining parts that execute different ophthalmologic examinations on the eye. In this embodiment, as ophthalmologic examinations, an eye-refractive-power examination, and an ocular-tension examination are employed particularly. Furthermore, it is also possible to configure to be capable of executing a cornea-shape examination, together with the eye-refractive-power examination or instead of the eye-refractive-power examination. Ophthalmologic examinations that can be executed by the ophthalmologic apparatus according to the present invention are not limited to the aforementioned ones, and may include any examination (measurement or photography) as exemplified below: visual acuity test, cornea-curvature examination, color-vision examination, visual-field examination, anterior segment, corneal endothelium photography, fundus oculi photography, OCT (Optical Coherence Tomography) examination, SLO (Scanning Laser Ophthalmoscope) examination, ultrasonic examination, radiation examination, and the like. Moreover, the number of the ophthalmologic examinations that can be executed by the ophthalmologic apparatus related to the present invention may also be an arbitrary number of more than two.

Figure 3:
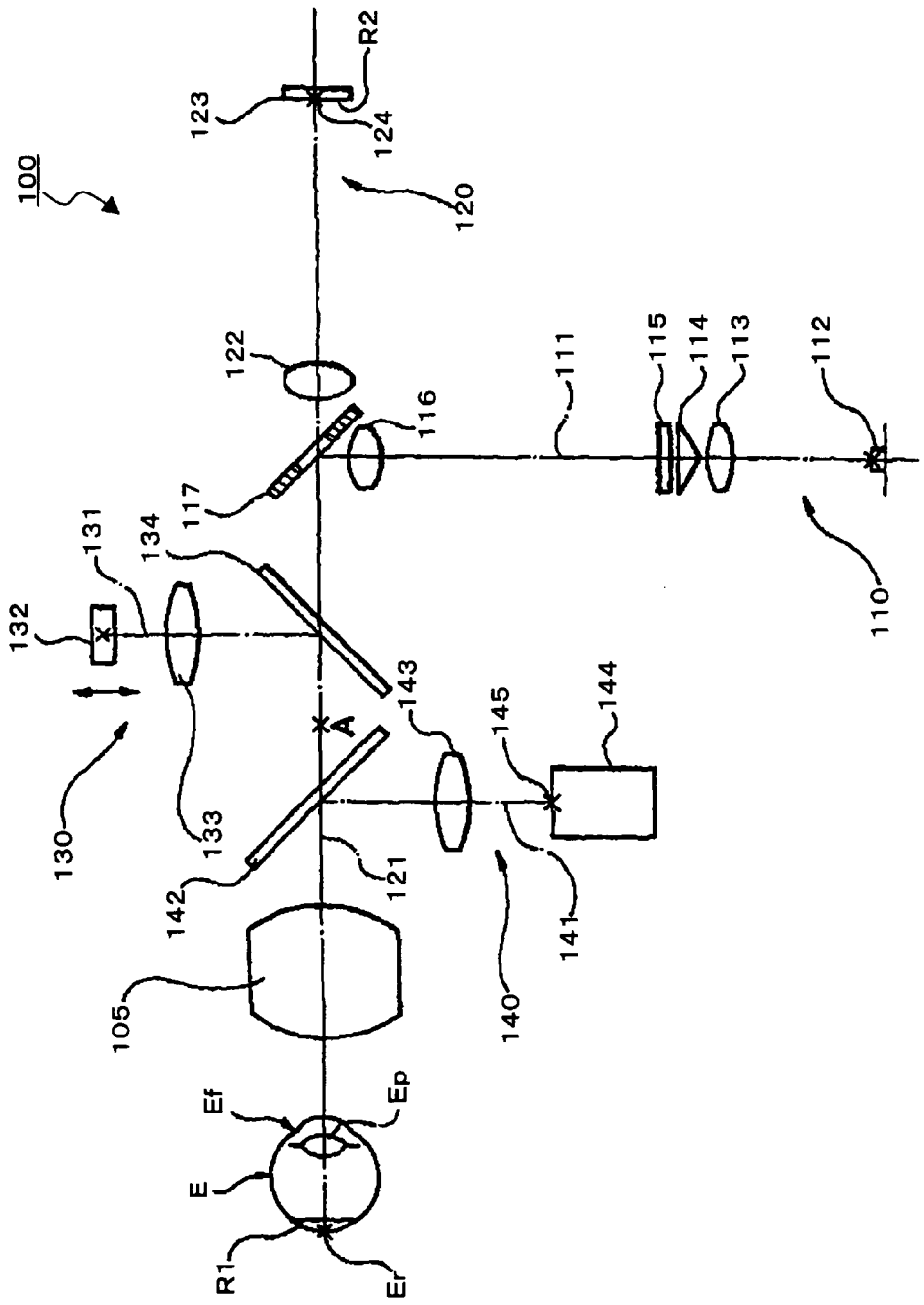
FIG. 3 is a schematic view showing an example of the configuration of an optical system in the embodiment of the ophthalmologic apparatus according to the present invention.
Figure 4:
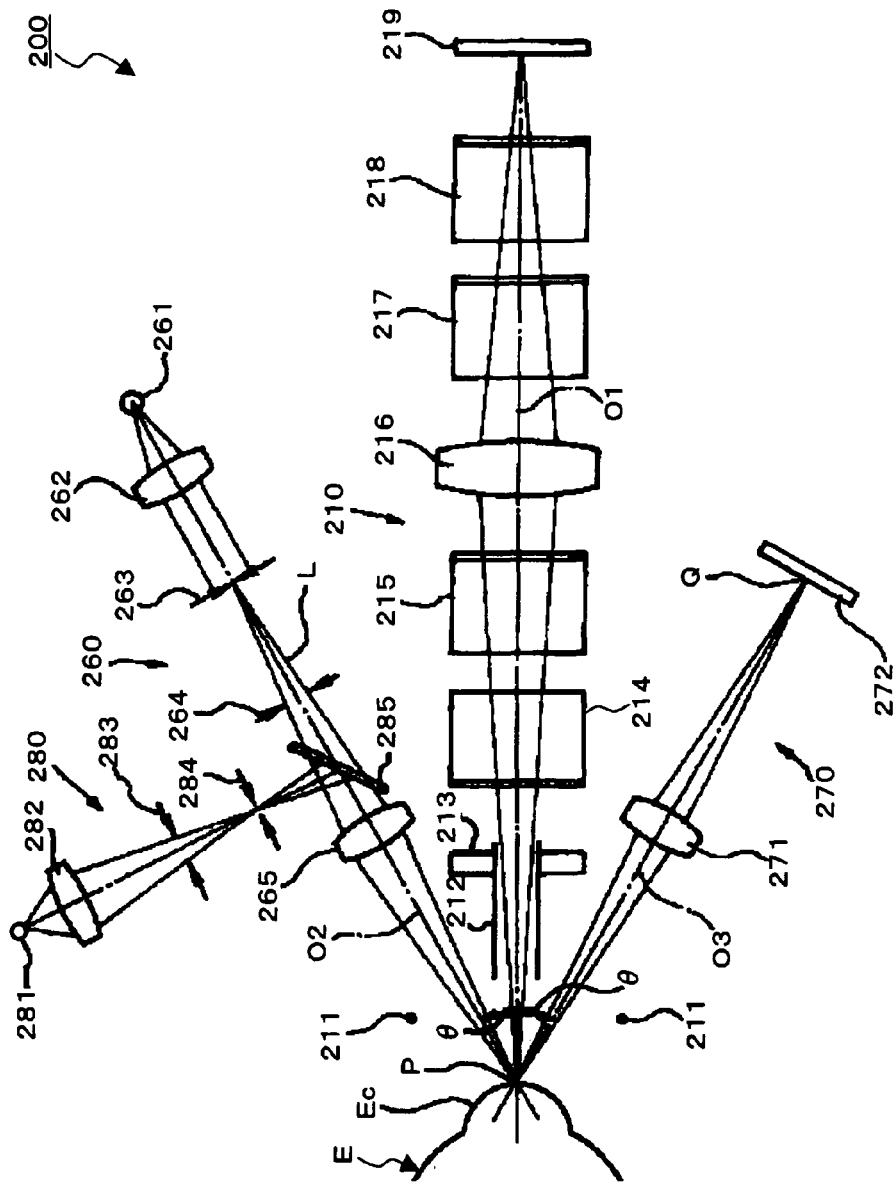
FIG. 4 is a schematic view showing an example of the configuration of the optical system in the embodiment of the ophthalmologic apparatus according to the present invention.
Figure 5:
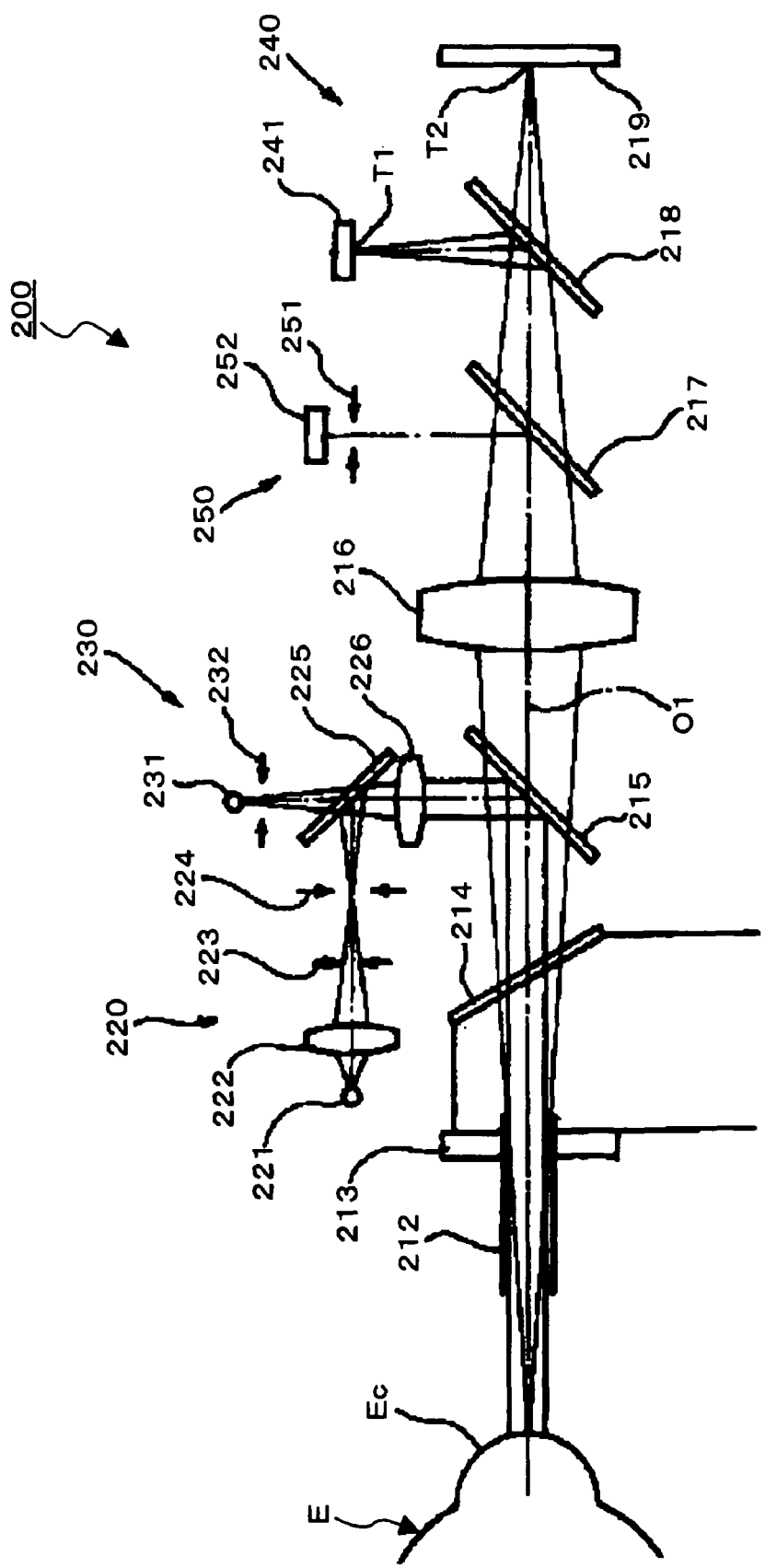
FIG. 5 is a schematic view showing an example of the configuration of the optical system in the embodiment of the ophthalmologic apparatus according to the present invention.

The configuration of an optical system housed in the measuring head 3 is shown in FIGS. 3 to 5. An eye-refractive-power measuring system 100 shown in FIG. 3 is an optical system for measuring the eye refractive power (spherical degree, degree of astigmatism, astigmatic axis angle, etc.) and cornea shape of an eye E. A tonometry system 200 shown in FIGS. 4 and 5 is an optical system for measuring the ocular tension of the eye E. The tonometry system 200 can also be used for measurement of the corneal thickness of the eye E. The measuring systems 100 and 200 each incorporates various kinds of optical elements, a drive mechanism, electric circuits, etc., in addition to the illustrated members (optical elements, etc.).

The eye-refractive-power measuring system 100 and the tonometry system 200 are housed in, for example, cases (not illustrated), respectively. The eye-refractive-power measuring system 100 and the tonometry system 200 are placed next to each other in the vertical direction, for example. In the present embodiment, it is assumed that the eye-refractive-power measuring system 100 is placed above and the tonometry system 200 is placed below.

{Eye-Refractive-Power Measuring System}

As shown in FIG. 3, the eye-refractive-power measuring system 100 has a configuration similar to that of a conventional eye-refractive-power measuring apparatus (refractometer) (refer to Japanese Patent No. 2937373, for example). Furthermore, similarly to a conventional corneal-shape-measuring apparatus (keratometer), the eye-refractive-power measuring system 100 may have a configuration for measuring the intermediate value of the corneal radius of curvature (average corneal refractive power) or the corneal radius of curvature (corneal refractive power) of the steep meridian/flat meridian (refer to, for example, Japanese Unexamined Patent Application Publication No. 8-229007). The apparatus described in this document has functions of both the refractometer and the keratometer.

The eye-refractive-power measuring system 100 includes an objective lens 105, a projecting system 110, an imaging system 120, a fixation-target projecting system 130, and an anterior-segment observing system 140. In addition thereto, optical elements for measuring the corneal shape may be disposed.

The projecting system 110 has an infrared LED (Light Emitting Diode) 112, a relay lens 113, a conic prism 114, a ring-shaped aperture diaphragm 115 and a relay lens 116, which are arranged along a reflected light axis 111 of an aperture mirror 117. The infrared LED 112 and the aperture mirror 117 are arranged so as to be conjugate with respect to the relay lenses 113 and 116. The aperture mirror 117 and a pupil Ep of the eye E are arranged so as to be conjugate with respect to the objective lens 105. Furthermore, the conic prism 114 and a fundus oculi Er are arranged so as to be conjugate with respect to the relay lens 116 and the objective lens 105.

The imaging system 120 includes optical elements arranged on and along an optical axis 121. A relay lens 122 and a CCD image sensor 123 are disposed on the optical axis 121 behind the aperture mirror 117. Assuming a position conjugate to the fundus oculi Er with respect to the objective lens 105 is denoted by symbol A, the position A and a light-receiving face 124 of the CCD image sensor 123 are conjugate to each other with respect to the relay lens 122.

The fixation-target projecting system 130 includes a fixation-target presenting part 132, a relay lens 133 and a dichroic mirror 134, which are arranged along an optical axis 131 branched out from a position on the optical axis 121 between the position A and the aperture mirror 117. The dichroic mirror 134 is obliquely disposed on the optical axis 121, and transmits an infrared light while reflecting a visible light. The fixation-target presenting part 132 is configured to be movable along the optical axis 131. The fixation-target presenting part 132 is placed at a conjugate position to the position A with respect to the relay lens 133.

The anterior-segment observing system 140 includes a half mirror 142, a relay lens 143 and an imaging device 144, which are arranged along an optical axis 141 branched out from a position on the optical axis 121 between the objective lens 105 and the position A. The half mirror 142 is obliquely disposed on the optical axis 121. The imaging device 144 includes a solid-state imaging element such as a CCD image sensor and a CMOS image sensor, an imaging tube, or the like. A light-receiving face 145 of the imaging device 144 is arranged so as to be conjugate to an anterior segment Ef with respect to the objective lens 105 and the relay lens 143.

The eye-refractive-power measuring system 100 may also have an alignment optical system for performing alignment of the measurement optical system with the eye E (position matching of the optical axis of the measurement optical system with the optical axis of the eye E). The measurement optical system is an optical system practically involved in the eye-refractive-power measurement, and is aligned with the optical axis of the objective lens 105 in this embodiment. As the alignment optical system, it is possible to apply a configuration described in Japanese Unexamined Patent Application Publication No. 2004-222955, for example. According to the configuration described in JP-A 2004-222955, it is possible to automatically perform the alignment (auto-alignment function).

Instead of such an optical system dedicated to the alignment, it is also possible to use a configuration described below to perform the alignment (e.g., Japanese Unexamined Patent Application Publication No. 2006-263082). The optical axis of the anterior-segment observing system 140 coincides with the optical axis of the measurement optical system (measurement optical axis), and the center position of the light-receiving face 145 coincides with the optical axis of the anterior-segment observing system 140. The anterior segment image of the eye E is acquired by the anterior-segment observing system 140, this anterior segment image is analyzed, and the optical axis position of the eye E is specified. Further, displacement of the aforementioned optical axis position with respect to the center position of a frame (corresponding to the center position of the light-receiving face 145) is obtained. Then, the eye-refractive-power measuring system 100 (measuring head 3) is moved so as to negate the displacement, whereby it is possible to make the optical axis of the measurement optical system coincide with the optical axis of the eye E.

A mode of measuring eye refractive power by the eye-refractive-power measuring system 100 will be described. It is assumed that the alignment of the eye-refractive-power measuring system 100 with the eye E is already completed. During the measurement, an image of the anterior segment Ef is acquired by the anterior-segment observing system 140. This image is displayed on the display 4, whereby it is possible to check whether the anterior segment Ef is placed in a proper position. Furthermore, a fixation target is projected to the fundus oculi Er by the fixation-target projecting system 130, whereby the eye is fixated in a foggy state.

The infrared LED 112 is turned on in this state, and a ring image R1 is formed on the fundus oculi Er. A fundus reflected light of the ring image R1 is projected to the light-receiving face 124 of the CCD image sensor 123. The CCD image sensor 123 detects a projected image (ring image R2). As in the conventional technique, the ophthalmologic apparatus 1 (eye-refractive-power calculator 41 in FIG. 6) obtains the eye refractive power of the eye E by analyzing the shape of the ring image R2.

{Tonometry System}

As shown in FIGS. 4 and 5, the tonometry system 200 is provided with a configuration similar to that of a conventional noncontact type tonometer (e.g., Japanese Unexamined Patent Application Publication No. 2002-102170). The tonometry system 200 includes an anterior-segment observing system 210, an XY-alignment target projecting system 220, a fixation-target projecting system 230, an XY-alignment detecting system 240, a corneal-deformation detecting system 250, a slit projecting system 260, a light-receiving system 270, and a Z-alignment target projecting system 280. Here, symbols X, Y and Z denote coordinate axes of a three-dimensional coordinate system. The X direction corresponds to the horizontal direction, the Y direction corresponds to the vertical direction, and the Z direction corresponds to the anteroposterior direction.

The anterior-segment observing system 210 includes a plurality of anterior-segment illumination light sources 211, an air-puff spraying nozzle 212, an anterior-segment window glass 213, a chamber window glass 214, a half mirror 215, an objective lens 216, half mirrors 217 and 218, and a CCD image sensor 219. The members 212 to 219 except the anterior-segment illumination light sources 211 are placed on an optical axis O1. The air-puff spraying nozzle 212 sprays air puff generated by a not-shown air compression mechanism toward the eye E.

The plurality of the anterior-segment illumination light sources 211 are placed on the right and left positions of the eye E, and directly illuminate the anterior segment. The illumination lights emitted from the anterior-segment illumination light sources 211 are reflected at the anterior segment of the eye E, are passed through the inside and outside of the air-puff spraying nozzle 212, are passed through the anterior-segment window glass 213, the chamber window glass 214 and the half mirror 215, and are converged by the objective lens 216. The converged light flux is transmitted by the half mirrors 217 and 218, and projected to the light-receiving face of the CCD image sensor 219.

The CCD image sensor 219 detects the projected image to capture an anterior segment image of the eye E.

The XY-alignment target projecting system 220 includes an alignment light source 221, a condenser lens 222, an aperture diaphragm 223, a pinhole plate 224, a dichroic mirror 225, and a projection lens 226. These members 221 to 226 are placed on an optical axis branched out from the optical axis O1 by the half mirror 215. The dichroic mirror 225 reflects an infrared light and transmits a visible light.

The alignment light source 221 emits an infrared light. This infrared light is passed through the aperture diaphragm 223 while being converged by the condenser lens 222, and is guided by the pinhole plate 224. The light flux passed through the pinhole plate 224 is reflected by the dichroic mirror 225 and collimated by the projection lens 226. This collimated light is reflected by the half mirror 215 and applied to the eye E along the optical axis O1. The emitted light is used as an XY-alignment target light for performing alignment in the XY direction.

The fixation-target projecting system 230 includes a fixation-target light source 231, a pinhole plate 232, and a projection lens 226, which are placed on an optical axis branched out from the optical axis O1 by the half mirror 215.

The visible light emitted by the fixation-target light source 231 is passed through the pinhole plate 232 and the dichroic mirror 225, and is collimated by the projection lens 226. This collimated light is reflected by the half mirror 215 and projected to the fundus oculi of the eye E along the optical axis O1. The reflected light is used as a fixation target.

The XY-alignment detecting system 240 includes a half mirror 218 and an optical sensor 241. The optical sensor 241 is composed of a sensor capable of position detection, such as a PSD (Position Sensitive Detector).

The XY-alignment target light applied to the eye E by the XY-alignment target projecting system 220 is reflected at the (surface of) the cornea Ec. The light reflected at the cornea is passed through the inside of the air-puff spraying nozzle 212, the anterior-segment window glass 213, the chamber window glass 214 and the half mirror 215, and is converged by the objective lens 216. The converged light transmitted by the half mirror 217 is split by the half mirror 218.

Components reflected by the half mirror 218 form a bright-point image T1 on the receiving face of the optical sensor 241.

Further, components transmitted by the half mirror 218 form a bright-point image T2 on the receiving face of the CCD image sensor 219.

The ophthalmologic apparatus 1 (e.g., a calculator 40 in FIG. 6) calculates misalignment of the tonometry system 200 in the XY direction with respect to the cornea Ec, based on the result of detection of the bright-point image T1 by the optical sensor 241. Meanwhile, the result of detection of the bright-point image T2 by the CCD image sensor 219 is displayed on the display 4 together with the anterior segment image of the eye E. Consequently, it is possible to visually check the state of the alignment in the XY direction.

The light flux reflected by the half mirror 217 is guided to the corneal-deformation detecting system 250, and detected by the optical sensor 252 through the pinhole plate 251. The optical sensor 252 is a sensor capable of detecting the amount of light such as a photodiode.

The optical sensor 252 detects the amount of the light reflected by the cornea Ec applanated by the air puff from the air-puff spraying nozzle 212. The ophthalmologic apparatus 1 (an ocular-tension calculator 43) obtains the amount of deformation of the cornea Ec from the detection result, thereby obtaining the value of the ocular tension of the eye E.

The slit projecting system 260 includes a slit light source 261, a condenser lens 262, a slit 263, a rectangular aperture diaphragm 264, a half mirror 285, and a projection lens 265. These members are placed on an optical axis O2. The slit 263 is placed so as to be conjugate to the rear face of the cornea Ec with respect to the projection lens 265.

The slit light source 261 emits an infrared light. This infrared light is converged by the condenser lens 262 and guided into the slit 263. The infrared light passed through the slit 263 (a slit light L) is passed through the rectangular aperture diaphragm 264 and the half mirror 285, and is projected to the cornea Ec by the projection lens 265.

The slit light L projected to the cornea Ec is reflected by the surface of the cornea and the rear face of the cornea.

The light-receiving system 270 includes an imaging lens 271 and a line sensor 272. These members are placed on an optical axis O3. The optical axes O2 and O3 are disposed so that each of them forms an angle θ with respect to the optical axis O1 in the opposite directions to each other in the horizontal direction.

The corneal reflected light of the slit light L (surface reflection, rear-face reflection) is converged by the imaging lens 271 to form an image on the light-receiving face of the line sensor 272. The ophthalmologic apparatus 1 (the calculator 40) obtains the light amount distribution of the corneal reflected light based on an output signal from the line sensor 272, and performs alignment in the Z direction based on this light amount distribution. Furthermore, the ophthalmologic apparatus 1 (a corneal-thickness calculator) obtains the thickness of the cornea Ec based on two peak positions in the light amount distribution of the corneal reflection light.

The Z-alignment target projecting system 280 includes an alignment light source 281, a condenser lens 282, an aperture diaphragm 283, a pinhole plate 284, a half mirror 285, and a projection lens 265. The pinhole plate 284 is placed in the focal position of the projection lens 265. The aperture diaphragm 283 is placed so as to be conjugate to a corneal apex P with respect to the projection lens 265.

The infrared light emitted from the alignment light source 281 is converged by the condenser lens 282 to reach the aperture diaphragm 283. Part of the infrared light passed through the aperture diaphragm 283 is passed through the pinhole plate 284 to be reflected by the half mirror 285 and projected to the cornea Ec by the projection lens 265.

The infrared light reflected at the (surface of the) cornea Ec is converged by the imaging lens 271 to form a bright-point image Q on the light-receiving face of the line sensor 272. The result of detection of this bright-point image Q is used for the alignment (rough adjustment) in the Z direction.

[Control System]

Figure 6:
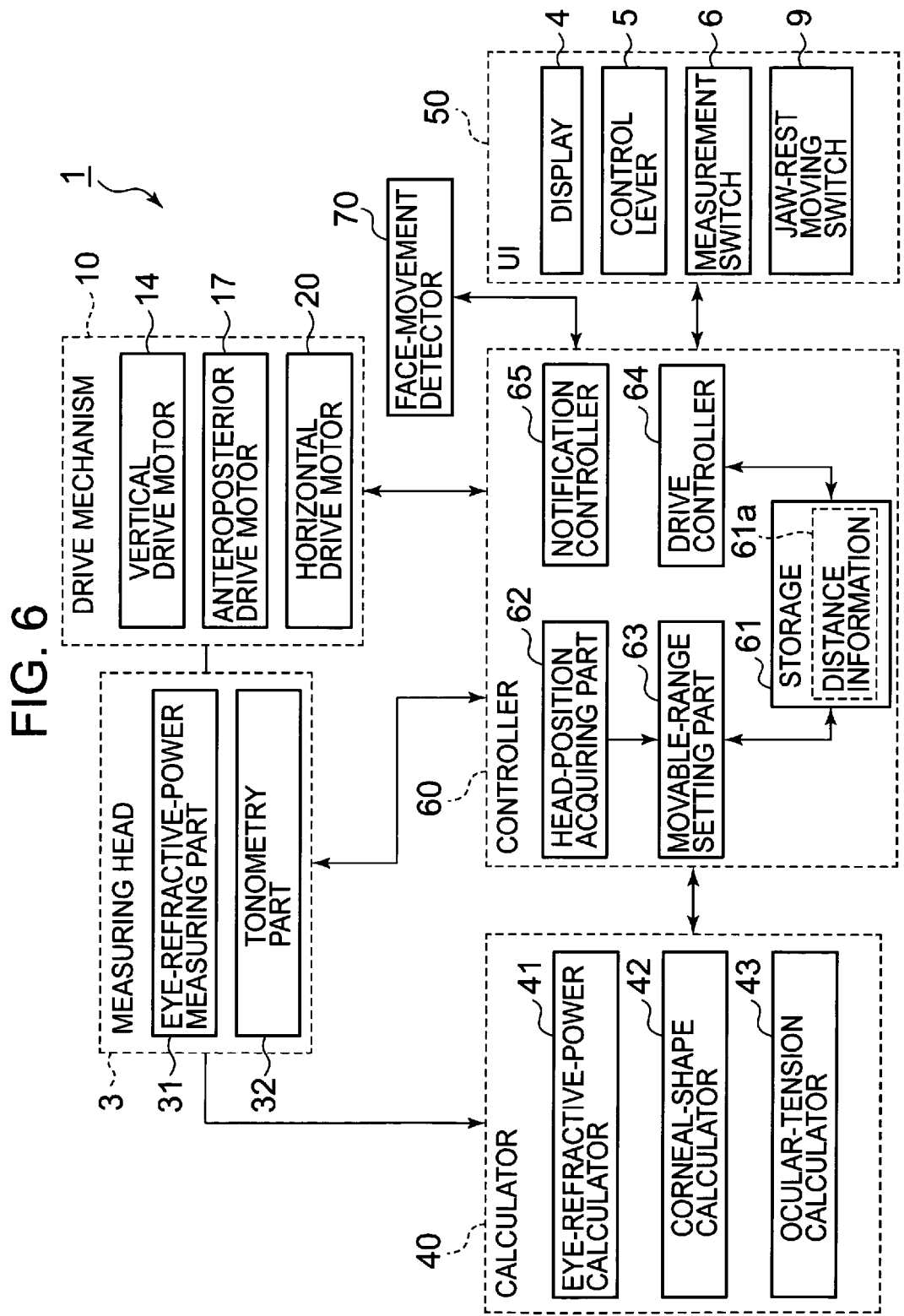
FIG. 6 is a schematic block diagram showing an example of the configuration of a control system in the embodiment of the ophthalmologic apparatus according to the present invention.

A configuration example of a control system of the ophthalmologic apparatus 1 is shown in FIG. 6.

{Measuring Head}

Each part of the measuring head 3 is controlled by a controller 60. The measuring head 3 has an eye-refractive-power measuring part 31 and a tonometry part 32. The eye-refractive-power measuring part 31 includes a configuration for measuring the eye refractive power of the eye E, such as the eye-refractive-power measuring system 100 shown in FIG. 3. The eye-refractive-power measuring part 31 may include a configuration for measuring the corneal shape. The tonometry part 32 includes a configuration for measuring the ocular tension of the eye E, such as the tonometry system 200 shown in FIGS. 4 and 5.

Further, the tonometry part 32 may be configured to be also capable measuring the corneal thickness of the eye E. Measurement by the eye-refractive-power measuring part 31 is executed at a predetermined working distance Dr. The working distance Dr may be set to 35 mm, for example. The working distances for the eye refractive power measurement and the corneal shape measurement are equal to each other as in the conventional art. Further, measurement by the tonometry part 32 is executed at a predetermined working distance Dt.

The working distance Dt may be set to 11 mm, for example. Here, the working distance Dt is set to be shorter than the working distance Dr. The eye-refractive-power measuring part 31 is an example of the "first examining part" of the present invention. Further, the tonometry part 32 is an example of the "second examining part" of the present invention. In general, the working distance is set in advance for each examination in accordance with the type of the examination, the configuration of the measurement optical system, etc.

The working distance can be set to a distance between the tip position of the measurement optical system and the eye E, or a distance between the eye E and the tip position (front face of the housing, etc.) of each examining part (the measuring parts 31 and 32). However, in this embodiment, the definition of the working distance is consistently used for the plurality of examining parts in order to take a difference of working distances into consideration.

{Drive Mechanism}

The drive mechanism 10 has the vertical drive motor 14, the anteroposterior drive motor 17, and the horizontal drive motor 20, which are shown in FIG. 2. The drive mechanism 10 is an example of the "driver" of the present invention.

{Calculator}

The calculator 40 calculates predetermined eye-characteristic information based on data obtained by the measuring head 3. The calculator 40 includes a microprocessor such as a CPU, a RAM, a ROM, a hard disk drive, etc. The calculator 40 has the refractive-power calculator 41, the corneal-shape calculator 42, and the ocular-tension calculator 43. The refractive-power calculator 41 calculates the eye refractive power (the spherical degree, degree of astigmatism, astigmatic axial angle, etc.) of the eye E based on data obtained by the eye-refractive-power measuring part 31. The corneal-shape calculator 42 calculates the corneal shape (average corneal refractive power, corneal refractive power, etc.) of the eye E based on data obtained by the eye-refractive-power measuring part 31. The ocular-tension calculator 43 calculates the value of ocular tension of the eye E based on data obtained by the tonometry part 32. The calculator 40 is also capable of calculating the corneal thickness of the eye E based on data obtained by the tonometry part 32. The aforementioned calculation processes are executed by the calculator 40 as in the conventional art.

{User Interface}

A user interface (UI) 50 includes a display device, an operation device, an input device, etc. Specifically, the user interface 50 includes the display 4, the control lever 5, the measurement switch 6, the jaw-rest moving switch 9, etc. In a case where a computer is connected to the ophthalmologic apparatus 1, the user interface 50 may include a display, a mouse, a keyboard, etc., of this computer.

{Controller}

The controller 60 controls each part of the ophthalmologic apparatus 1. The controller 60 includes a microprocessor such as a CPU, a RAM, a ROM, a hard disk drive, etc. The controller 60 has a storage 61, a head-position acquiring part 62, a movable-range setting part 63, a drive controller 64, and a notification controller 65.

(Storage)

The storage 61 stores various kinds of information on control of the ophthalmologic apparatus 1. Specifically, the storage 61 stores information on control of the drive mechanism 10, such as distance information 61a. The storage 61 is an example of the "storage" of the present invention.

The distance information 61a includes the working distance Dt for measurement by the tonometry part 32 and the working distance Dr for measurement by the eye-refractive-power measuring part 31. In general, the distance information 61a includes a working distance for measurement by each of the plurality of examining parts. Each working distance is set in advance, and is previously stored in the storage 61 as the distance information 61a. The distance information 61a may include a difference between these working distances Dr and Dt (ΔD=Dr−Dt), instead of the working distances Dr and Dt. Further, the distance information 61a includes a safe distance Ds in an examination with the tonometry part 32. The safe distance Ds represents a distance at which (the air-puff spraying nozzle 212 of) the tonometry part 32 can be the closest to the eye E during the measurement of the ocular tension, i.e., the shortest distance from the eye E when the tonometry part 32 is moved in the anteroposterior direction in the measurement of ocular tension. The safe distance Ds is set to at least a distance at which the tonometry part 32 does not come in contact with the eye E.

For example, the safe distance Ds is set to 6 mm. The safe distance Ds is properly set beforehand.

(Head-Position Acquiring Part)

The head-position acquiring part 62 acquires the position information of the measuring head 3 at the current moment. In a case where the eye-refractive-power measuring part 31 and the tonometry part 32 are configured to be independently movable, the head-position acquiring part 62 acquires the position information of each of the measuring parts 31 and 32 at the current moment. Specifically, the head-position acquiring part 62 is configured to acquire anteroposterior position information of the measuring head 3.

An example of a method of acquiring the position information of the measuring head 3 will be described. As a first example, there is a method of acquiring the position information of the measuring head 3 based on the content of control of the drive mechanism 10 by the drive controller 64. The drive mechanism 10 operates in response to a control signal from the drive controller 64. That is to say, each of the drive motors 14, 17 and 20 (including the stepping motors) receives pulse signals from the drive controller 64, and moves the measuring head 3 by a distance in accordance with the number of the pulses. A moving distance corresponding to a single pulse is set in advance.

Furthermore, in a case where the measuring head 3 is placed at a predetermined initial position at the time of, for example, start of an examination, it is possible to acquire three-dimensional position information of the measuring head 3 at the current moment by referring to the history of control signals transmitted by the drive controller 64 from a state where the measuring head 3 is placed in the initial position to the current moment. The initial position of the measuring head 3 can be set appropriately. For example, the initial position can be manually set by the user. Furthermore, it is possible to specify the pupillary distance (by inputting, selecting, etc.) and set a position corresponding to a value of half the pupillary distance as the initial position.

As a second example, there is a method of actually detecting the position of the measuring head 3. In other words, it is a method of acquiring the position information of the measuring head 3 by disposing a sensor (a potentiometer etc.) that detects the position of the measuring head 3.

By the aforementioned methods, the head-position acquiring part 62 acquires position information of the eye-refractive-power measuring part 31 (the measuring head 3) specifically when measurement of the eye refractive power (measurement of the corneal shape) is executed.

The head-position acquiring part 62 sends the acquired position information to the movable-range setting part 63.

(Movable-Range Setting Part)

The movable-range setting part 63 receives position information from the head-position acquiring part 62, and reads out the distance information 61a from the storage 61. Then, the movable-range setting part 63 sets a movable range of the tonometry part 32 (the measuring head 3) in a direction of the working distance Dt, based on this position information and the working distances Dr and Dt (or the difference ΔD between the working distances Dr and Dt). In this embodiment, the direction of the working distance Dt is the anteroposterior direction. The movable range represents a range within which movement of the tonometry part 32 (measuring head 3) in the anteroposterior direction is allowed. The movable range includes at least the boundary position toward the anterior direction (toward the eye E).

Figure 7:
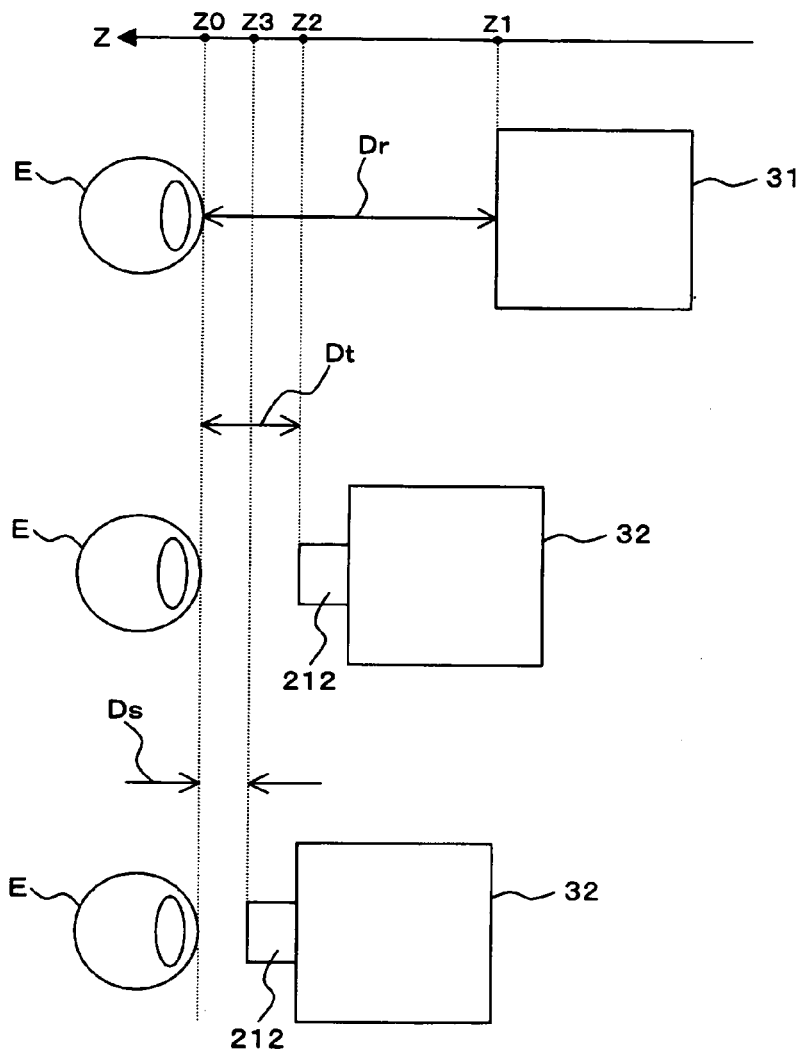
FIG. 7 is a schematic explanatory view for explaining a process executed in the embodiment of the ophthalmologic apparatus according to the present invention.

An example of a process of setting the movable range will be described with reference to FIG. 7. The eye-refractive-power measuring part 31 measures the eye refractive power at a position away from the eye E by the working distance Dr. Further, the tonometry part 32 measures the ocular tension at a position away from the eye E by the working distance Dt. Symbol Ds represents the safe distance in ocular-tension measurement as mentioned above. The movable-range setting part 63 calculates a Z coordinate value Z3 corresponding to the safe distance Ds for tonometry based on a Z coordinate value Z1 of the eye-refractive-power measuring part 31 at the time of measurement of the eye refractive power and information registered in the distance information 61a. This calculation process will be described below. The working distance Dr corresponds to a difference between a Z coordinate value Z0 of the eye E in eye-refractive-power measurement and the Z coordinate value Z1 of the eye-refractive-power measuring part 31 (Dr=Z0−Z1). Further, the working distance Dt corresponds to a difference between the Z coordinate value Z0 of the eye E in tonometry and a Z coordinate value Z2 of the tonometry part 32 (Dt=Z0−Z2). Here, the Z coordinate value Z0 of the eye E is unknown until position information at the time of eye-refractive-power measurement is acquired by the head-position acquiring part 62.

Further, it is assumed that the position of the eye E at the time of eye-refractive-power measurement is equal to the position of the eye E at the time of tonometry. A case where the eye E moves after eye-refractive-power measurement and before tonometry will be described later. Now, the movable-range setting part 63 first calculates the Z coordinate value Z2 corresponding to the working distance Dt in the examination by the tonometry part 32 based on the Z coordinate value Z1 and the working distances Dr and Dt. It is possible to calculate the Z coordinate value Z2 by an arithmetic expression "Z2=Z1+Dr−Dt" as apparent from FIG. 7. In addition, the movable-range setting part 63 calculates the aimed Z coordinate value Z3 by an arithmetic expression "Z3=Z2+Dt−Ds."

The Z coordinate values Z2 and Z3 are obtained in steps in the above calculation example, but it is also possible to employ another calculation method. For example, when the above-described two arithmetic expressions are combined, an arithmetic expression "Z3=Z1+Dr−Ds" can be obtained. In other words, without referring to the working distance Dt in tonometry, it is possible to obtain the Z coordinate value Z3 corresponding to the safe distance. In the case of employing this calculation method, it is not necessary to make the distance information 61a include the working distance Dt. However, it is thought to be desirable that the distance information 61a includes the working distance Dt, in order to determine the initial position in the anteroposterior direction of the measuring head 3 at the time of shift from eye-refractive-power measurement to tonometry.

According to the ophthalmologic apparatus of the present embodiment, alignment with an actual eye is executed at the time of eye-refractive-power measurement to place the eye-refractive-power measuring part 31 so that a distance from the actual eye exactly becomes the working distance Dr (placement of the eye-refractive-power measuring part 31 at an examination position for the actual eye will be described in detail later in "Operation"), it is possible to acquire accurate position information based on the actual eye. Then, the Z coordinate values Z2 and Z3 are calculated based on the accurate position information of the eye-refractive-power measuring part 31.

Therefore, it is possible to move the tonometry part 32 by a distance of the working distance Dt based on the distance to the current eye, and it becomes possible to move the tonometry part 32 within a safe movable range based on the position of the actual eye.

By the process described above, of the movable range, the shortest distance to the eye E, i.e., the closest distance (the most advanced distance) to the eye E is set. Meanwhile, it is also possible to set the farthest distance from the eye E (the most retracted distance).

For example, considering the adjustment width in the Z direction of the tonometry part 32, it is possible to set a position Dt−Ds away on the side opposite to the eye E with respect to a position corresponding to the working distance Dt as the most retracted distance. Furthermore, in consideration of eyelid opening, it is also possible to set the most retracted distance (e.g., a few cm to as much as 10 cm). Furthermore, the most retracted distance may be set, by the drive mechanism 10, corresponding to the most retracted position of the tonometry part 32.

Only the most advanced distance may be set without setting the most retracted distance.

The movable-range setting part 63 composes an example of the "setting part" of the present invention together with the head-position acquiring part 62. Note that the method of setting the movable range is not limited to the examples above.

(Drive Controller)

The controller 64 individually controls the motors 14, 17 and 20 of the drive controller 10, thereby moving the measuring head 3 in the vertical direction, the anteroposterior direction and the horizontal direction, respectively. Specifically, the drive controller 64 controls to move the tonometry part 32 (the measuring head 3) only within the movable range set by the movable-range setting part 63. For this, as explained for the head-position acquiring part 62, the drive controller 64 acquires the position information (specifically the position in the anteroposterior direction (Z direction)) of the tonometry part 32 based on the content of control on the drive mechanism 10, and prohibits movement beyond the movable range with reference to this position information. The head-position acquiring part 62 may be configured to acquire the position information of the tonometry part 32 at a proper timing and send the position information to the drive controller 64 so as to control to prohibit movement of the tonometry part 32 beyond the movable range.

(Notification Controller)

The notification controller 65 controls to output predetermined notification information when movement of the face of the subject retained by the jaw rest 7 and the forehead rest 8 occurs after execution of the eye-refractive-power measurement and before execution of the tonometry on the eye E. The movement of the face of the subject is detected by a face-movement detector 70. The face-movement detector 70 functions, for example, to detect that the face is away from the jaw rest 7 and/or the forehead rest 8. Moreover, the face-movement detector 70 may be configured to detect the movement of the position of the face in contact with the jaw rest 7 and/or the forehead rest 8.

A configuration example of the face-movement detector 70 will be described. As a first example, a microsensor or an ON/OFF sensor like a switch is disposed at a position of each of the jaw rest 7 and/or the forehead rest 8 coming in contact with the face of the subject, and the movement of the face can be thereby detected. As a second example, the anterior segment of the subject is photographed, and the movement of the face can be detected based on the position of the photographed image in the frame. As a third example, an infrared oscillator and an infrared receiver are arranged so as to face each other on the respective sides of the face of the subject, and the movement of the face can be detected. The configuration of the face-movement detector 70 is not limited to these examples, and any configuration capable of detecting the movement of the face retained by the jaw rest 7 and the forehead rest 8 may be applied. The notification information is outputted in a form recognizable by the operator, such as visual information and auditory information. The visual information is, for example, message information displayed on the display 4. The message information may be character-string information or may be image information. As the character-string information, information like "The subject's face has moved" or "Please adjust the position of the measuring head" is outputted. As the image information, information like an exclamation mark is outputted. On the other hand, the auditory information is, for example, an alarm and a voice message. It is generally preferred that the notification information includes information that the subject's face has moved or information for prompting adjustment of the position of the measuring head 3.

(Operation)

The operation of the ophthalmologic apparatus 1 according to this embodiment will be described. A flowchart of FIG. 8 shows an example of the operation of the ophthalmologic apparatus 1. In the operation shown in FIG. 8, a process of detecting the movement of the face of the subject is omitted. A case of executing this process will be separately described later.

In an ophthalmologic examination with the ophthalmologic apparatus 1, a plurality of examinations are executed on the right and left eyes in accordance with a predetermined examination flow. As an example of the examination flow, the examinations are executed in the following order: (1) eye-refractive-power measurement and corneal-shape measurement of the right eye; (2) eye-refractive-power measurement and corneal-shape measurement of the left eye; (3) tonometry (and corneal-thickness measurement) of the left eye; and (4) tonometry (and corneal-thickness measurement) of the right eye. The reason for executing the eye-refractive-power measurement before the tonometry will be described below. In a case where the tonometry is executed before the eye-refractive-power measurement, the measurement result may have an error because the eye-refractive-power measurement is executed after the cornea is deformed (applanated) by the air puff. The examination flow by the ophthalmologic apparatus 1 is not limited to the one described above. However, it is desirable to execute the tonometry after the eye-refractive-power measurement on the eye E (may be both the eyes, or may be one of the eyes).

First, the face of the subject is retained by the jaw rest 7 and forehead rest 8, and the operator instructs to start the examination (S1).

This instruction may be, for example, an operation of turning on the power supply of the ophthalmologic apparatus 1 or an operation of designating the subject (e.g., inputting the patient ID). Further, the operator may instruct to start the examination by operating an operation part (hardware key or software key) for instructing to start the examination disposed to the user interface 50.

In response to the instruction to start the examination, the drive controller 64 controls the drive mechanism 10 to move the eye-refractive-power measuring part 31 to an examination position for the right eye of the subject (S2). The examination position means a position of the eye-refractive-power measuring part 31 (or the tonometry part 32) in the aligned state with the eye E. In this state, the eye-refractive-power measuring part 31 (or the tonometry part 32) is placed in a position away from the eye E by the working distance Dr (or the working distance Dt).

The process in step 2 is executed in the following manner, for example. First, the drive controller 64 controls the drive mechanism 10 to vertically move the measuring head 3 and move the eye-refractive-power measuring part 31 to a predetermined height position. The height position is, for example, equivalent to a standard height at the time of executing the eye-refractive-power measurement, and is set beforehand.

Next, the drive controller 64 controls the drive mechanism 10 to horizontally move the measuring head 3 and place the measuring head 3 at a predetermined initial position. This initial position is, for example, an origin position of each of the X and Y directions set beforehand. This origin is, for example, set to a center position of the movable range of the measuring head 3 in each of the X and Y directions.

Next, the drive controller 64 controls to move the measuring head 3 (eye-refractive-power measuring part 31) to an examination position for the eye-refractive-power measurement of the right eye of the subject. At this moment, the working distance Dr included in the distance information 61a is referred to. This process can be full-automatically or semi-automatically executed in the following manner, for example.

As an example of the full-automatic process, the drive controller 64 controls to move the measuring head 3 in the right-eye direction by a predetermined distance (for example, half the pupillary distance), and the eye-refractive-power measuring part 31 is placed at the examination position for the right eye by execution of the alignment as conventional. The pupillary distance may be acquired in advance from the subject, or a standard value may be applied. It is also possible to configure to move the measuring head 3 until the right eye is detected while photographing images of the subject.

As an example of the semi-automatic process, the operator operates the control lever 5 to move the measuring head 3 to a position facing the right eye and place the eye-refractive-power measuring part 31 at the examination position for the right eye by execution of alignment as conventional.

Next, the eye-refractive-power measurement and the corneal-shape measurement of the right eye are executed (S3). This process is executed in a manner that, as conventional, the eye-refractive-power measuring part 31 acquires data of the right eye, the eye-refractive-power calculator 41 calculates the eye refractive power of the right eye based on the data, and the corneal-shape calculator 42 calculates the corneal shape of the right eye. The examination may be automatically started in response to completion of the alignment, or may be manually started by the operator operating the measurement switch 6, for example. The results of the eye-refractive-power measurement and the corneal-shape measurement are stored into the storage 61.

The head-position acquiring part 62 acquires the position information of the eye-refractive-power measuring part 31 (measuring head 3) at the time of execution of the eye-refractive-power measurement, etc., of the right eye (S4). The movable-range setting part 63 receives the position information and reads out the distance information 61a from the storage 61. Then, the movable-range setting part 63 calculates the movable range of the tonometry part 32 in the tonometry of the right eye based on the position information and the distance information 61a (S5). The movable-range setting part 63 registers the results of the calculation of the movable range into the storage 61.

Next, the drive controller 64 controls the drive mechanism 10 to move the measuring head 3 and place the eye-refractive-power measuring part 31 at the examination position for the left eye (S6). At this moment, it is desirable to move the measuring head 3 toward the left eye while making it retract from the subject in order to avoid contact with the nose, etc., of the subject. The process in step 6 can be performed similarly in step 2, for example.

Next, the eye-refractive-power measurement and corneal-shape measurement of the left eye are executed (S7). The measurement results of the eye refractive power and the corneal shape are stored into the storage 61.

The head-position acquiring part 62 acquires the position information of the eye-refractive-power measuring part 31 (measuring head 3) at the time of execution of the eye-refractive-power measurement, etc., of the left eye (S8). The movable-range setting part 63 calculates the movable range of the tonometry part 32 for the tonometry of the left eye based on the position information and the distance information 61a (S9).

Next, the drive controller 64 controls the drive mechanism 10 to move the tonometry part 32 to the examination position for the left eye of the subject (S10). This process is executed by, for example, controlling the vertical drive motor 14 to move the measuring head 3 vertically (upwardly in this embodiment) and place the tonometry part 32 in front of the left eye, and moreover, executing alignment as conventional to place the tonometry part 32 to the examination position for the left eye.

In this alignment, the drive mechanism 10 moves the tonometry part 32 in the anteroposterior direction only within the movable range obtained in step 9. Further, also in a case where the operator uses the control lever 5 to move the tonometry part 32, the drive mechanism 10 moves the tonometry part 32 in the anteroposterior direction only within the movable range obtained in step 9. In other words, even if an instruction to move beyond the movable range is inputted, the drive mechanism 10 acts so as to ignore this instruction. With regard to the movement in the direction retracting from the eye E (the rear direction), it is possible to configure to be capable of overriding the limits of the movable range.

When the alignment is completed, the tonometry part 32 executes the tonometry on the left eye (S11). This process is executed in such a manner that the tonometry part 32 acquires data of the left eye and the ocular-tension calculator 43 analyzes the data to calculate the ocular tension of the left eye. As well as the tonometry, the corneal-thickness measurement may be executed. Further, the tonometry may be started automatically in response to the completion of the alignment, or may be started manually by the operator operating the measurement switch 6, for example. The measurement results of the ocular tension are stored in the storage 61.

Next, the drive controller 64 controls the drive mechanism 10 to move the measuring head 3 and place the tonometry part 32 to the examination position for the right eye (S12). This process can be executed similarly in step 6, for example. Further, in this process, the alignment as conventional is also executed. Here, the drive mechanism 10 moves the tonometry part 32 in the anteroposterior direction only within the movable range obtained in step 5.

When the alignment is completed, the tonometry part 32 executes the tonometry on the right eye (S13). The measurement results of the ocular tension are stored in the storage 61. This concludes the description of the operation shown in FIG. 8.

Next, an operation of the ophthalmologic apparatus 1 in the case of detecting the movement of the face of the subject will be described with reference to a flowchart shown in FIG. 9. An examination on a single eye E will be described below, but the same process is executed in the examination on both the eyes as in FIG. 8.

First, the face of the subject is retained by the jaw rest 7 and the forehead rest 8, and the operator instructs to start the examination (S21).

In response to the instruction to start the examination, the drive controller 64 controls the drive mechanism 10 to move the eye-refractive-power measuring part 31 to the examination position for the eye E (S22). Subsequently, the eye-refractive-power measurement and the corneal-shape measurement of the eye E are executed (S23). The measurement results are stored in the storage 61.

When the eye-refractive-power measurement, etc., are completed, the controller 60 controls the face-movement detector 70 to start detection of the movement of the face of the subject (S24). The detecting operation may be started before the measurement in step 23.

Next, the head-position acquiring part 62 acquires the position information of the eye-refractive-power measuring part 31 (measuring head 3) at the time of execution of the eye-refractive-power measurement, etc., of the eye E (S25). The movable-range setting part 63 calculates the movable range of the tonometry part 32 in the tonometry on the eye E based on the position information and the distance information 61a (S26).

Next, the drive controller 64 controls the drive mechanism 10 to move the measuring head 3 and place the tonometry part 32 at the examination position for the eye E (S27). In this process, alignment is executed as conventional. At this moment, the drive mechanism 10 moves the tonometry part 32 in the anteroposterior direction only within the movable range obtained in Step 26.

In a case where the movement of the face of the subject is not detected by the face-movement detector 70 between Step 24 and this stage (S28: No), the tonometry part 32 executes the tonometry on the eye E (S29). The measurement result of the ocular tension is stored in the storage 61. This is the end of the operation in this case.

On the other hand, in a case where the movement of the face is detected between Step 24 and this stage (S28: Yes), the notification controller 65 outputs the notification information (S30). At this moment, the drive controller 64 discards the movable range obtained in Step 26. In other words, the drive controller 64 eliminates the restriction of the movement range of the tonometry 32 by the aforementioned movable range.

The operator acknowledges the movement of the face of the subject based on the outputted notification information, and properly adjusts the position of the tonometry part 32 with respect to the eye E (S31). The alignment with respect to the eye E may be performed automatically again. After the adjustment of the position, the tonometry part 32 executes the tonometry on the eye E in response to, for example, an instruction by the operator (S29). The measurement result of the ocular tension is stored in the storage 61. This is the end of the description of the operation shown in FIG. 9.

[Actions and Effects]

As described above, the ophthalmologic apparatus 1 is an apparatus capable of executing the eye-refractive-power measurement (and the corneal-shape measurement) and the tonometry. Here, the working distance in the tonometry is set shorter than the working distance in the eye-refractive-power measurement. Further, the ophthalmologic apparatus 1 is provided with the drive mechanism 10 that moves the measuring head 3 having the eye-refractive-power measuring part 31 and the tonometry part 32, and is configured to execute the tonometry after executing the eye refractive power by changing the position of the measuring head 3 with respect to the eye E.

Furthermore, the ophthalmologic apparatus 1 stores the distance information 61a in advance. The distance information 61a includes a distance between the eye E and the examining part in the eye-refractive-power measurement and the tonometry. Specifically, the distance information 61a includes the working distance Dr for the eye-refractive-power measurement and the safe distance Ds from the eye E for moving the tonometry part 32 in the anteroposterior direction in the tonometry. The distance information 61a may further include the working distance Dt for the tonometry.

The ophthalmologic apparatus 1 acquires the position information of the eye-refractive-power measuring part 31 at the time of execution of the eye-refractive-power measurement on the eye E and, based on the position information and the distance information 61a, sets the movable range of the tonometry part 32 in the direction of the working distance Dt (the anteroposterior direction, the Z direction) for the tonometry. Then, in the tonometry, the ophthalmologic apparatus 1 moves the tonometry part 32 in the anteroposterior direction only within this movable range.

According to the ophthalmologic apparatus 1, it is possible to increase safety by automatically setting the movable range of the measuring head 3. More specifically, according to the ophthalmologic apparatus 1, in the tonometry, it is possible to prevent the air-puff spraying nozzle 212 from coming in contact with the eye E. Further, according to the ophthalmologic apparatus 1, there is no need to manually set the movable range of the measuring head 3, so that it is possible to solve a problem such as a drop in examination efficiency and a cumbersome operation. Specifically, this is useful when examining both the right and left eyes. Further, situations such as forgetting to set the movable range or completely omitting the setting of the movable range in favor of optimizing the examination efficiency may be avoided. In other words, according to the ophthalmologic apparatus 1, it is possible to effectively increase the safety in the subject.

Further, according to the ophthalmologic apparatus 1, as described with reference to FIG. 8, when automatically executing the eye-refractive-power measurement and the tonometry on both the eyes, it is possible to increase the safety in the eye.

Further, as described with reference to FIG. 9, the ophthalmologic apparatus 1 is configured to output the notification information when the movement of the face of the subject is detected between the eye-refractive-power measurement and the tonometry. If the face of the subject moves between the eye-refractive-power measurement and the tonometry, there is a fear that the tonometry part 32 comes in contact with the subject even when being moved within the movable range. According to the ophthalmologic apparatus 1, it is possible to notify such a fear, so that it is possible to further increase safety.

The aforementioned configurations are merely examples for implementing the ophthalmologic apparatus according to the invention.

Those who attempt to implement the present invention may make appropriate optional modifications within the scope of the present invention.

What is claimed is:

1. An ophthalmologic apparatus that has a first examining part executing a first examination on an eye at a first working distance, a second examining part executing a second examination on the eye at a second working distance shorter than the first working distance, and a driver moving the first examining part and the second examining part, and that executes the second examination after executing the first examination, the ophthalmologic apparatus comprising:
    a storage configured to previously store distance information including the first working distance and a distance between the second examining part and the eye in the second examination;
    a setting part configured to acquire position information of the first examining part at the time of execution of the first examination, and set a movable range of the second examining part in a direction of the second working distance based on the position information and the distance information;
    a controller configured to control the driver to move the second examining part within the movable range; and
    a restriction part configured to restrict the movement of the second examination part to the moveable range set by the setting part.

2. The ophthalmologic apparatus according to claim 1, wherein:
    the distance information includes a shortest distance to the eye at the time of movement of the second examining part by the driver in the second examination.

3. The ophthalmologic apparatus according to claim 2, wherein:
    the setting part calculates a value derived by subtracting the shortest distance from a sum of the position information and the first working distance, and sets the movable range based on the calculated value.

4. The ophthalmologic apparatus according to claim 3, wherein:
    the distance information further includes the second working distance; and
    after execution of the first examination, based on the position information, the first working distance and the second working distance, the controller controls the driver to move the second examining part to a position separated from the eye by the second working distance.

5. The ophthalmologic apparatus according to claim 3, wherein:
    the second examining part executes tonometry on the eye as the second examination.

6. The ophthalmologic apparatus according to claim 3, wherein:
    the first examining part executes eye-refractive-power measurement and/or corneal-shape measurement on the eye as the first examination.

7. The ophthalmologic apparatus according to claim 3, further comprising:
    a retaining part configured to retain a face of a subject;
    a detector configured to detect movement of the face retained by the retaining part; and
    a notifying part configured to output notification information when movement of the face is detected by the detector during a period after execution of the first examination and before execution of the second examination.

8. The ophthalmologic apparatus according to claim 7, wherein:
    the controller discards the movable range set by the setting part when movement of the face is detected by the detector during a period after execution of the first examination and before execution of the second examination.

9. The ophthalmologic apparatus according to claim 2, wherein:
    the distance information further includes the second working distance; and
    after execution of the first examination, based on the position information, the first working distance and the second working distance, the controller controls the driver to move the second examining part to a position separated from the eye by the second working distance.

10. The ophthalmologic apparatus according to claim 1, wherein:
    the second examining part executes tonometry on the eye as the second examination.

11. The ophthalmologic apparatus according to claim 1, wherein:
    the first examining part executes eye-refractive-power measurement and/or corneal-shape measurement on the eye as the first examination.

12. The ophthalmologic apparatus according to claim 1, further comprising:
    a retaining part configured to retain a face of a subject;
    a detector configured to detect movement of the face retained by the retaining part; and
    a notifying part configured to output notification information when movement of the face is detected by the detector during a period after execution of the first examination and before execution of the second examination.

13. The ophthalmologic apparatus according to claim 12, wherein:

the controller discards the movable range set by the setting part when movement of the face is detected by the detector during a period after execution of the first examination and before execution of the second examination.

* * * * *